US00PP31399P2

(12) United States Plant Patent
Hansen

(10) Patent No.: US PP31,399 P2
(45) Date of Patent: Jan. 21, 2020

(54) ***SALVIA* PLANT NAMED 'BUMBLESNOW'**

(50) Latin Name: ***Salvia nemorosa* (Linnaeus)**
Varietal Denomination: Bumblesnow

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,483

(22) Filed: Nov. 20, 2018

(51) Int. Cl.
*A01H 5/02* (2018.01)
*A01H 6/00* (2018.01)

(52) U.S. Cl.
USPC ..... Plt./475

(58) Field of Classification Search
USPC ..... Plt./475
CPC ..... A01H 6/00; A01H 5/02
See application file for complete search history.

*Primary Examiner* — Keith O. Robinson

(57) ABSTRACT

A new and distinct cultivar of perennial *Salvia* plant named 'Bumblesnow' characterized by its small white-colored flowers densely arranged in tight verticils, with compact upright habit. Flower stems are heavily-branched with branches closely arranged. 'Bubblesnow' has strong vigorous growth rate, small gray-green foliage and is winter-hardy. *Salvia* 'Bumblesnow' is especially useful for landscaping and containerized ornamentals by itself or in combination with other plants.

1 Drawing Sheet

Botanical denomination: *Salvia nemorosa* (Linnaeus).
Cultivar designation: 'Bumblesnow'.

CROSS REFERENCE TO RELATED APPLICATIONS

*Salvia* plant named 'Bumbleberry' U.S. Plant patent application Ser. No. 15/731,913

*Salvia* plant named 'Bumbleblue' U.S. Plant Pat. No. 30,084

*Salvia* plant named 'Bumblesky' U.S. Plant Pat.t No. 30085

STATEMENT REGARDING PRIOR DISCLOSURES UNDER 37 CFR 1.77(b)(6)

The first public disclosure of the claimed plant, in the form of a sale, was made by Walters Gardens, Inc. on Jul. 9, 2018. Prior to that, on Nov. 28, 2017 the claimed plant was displayed as a photograph without description in a calendar distributed to customers of Walters Gardens, Inc., who obtained the plant and all information relating thereto, from the inventor. No plants of *Salvia* 'Bumblesnow' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of ornamental sage plant hereinafter referred to by the cultivar name *Salvia* 'Bumblesnow' or as the new plant. The new plant was selected from an insect-pollinated cross between the female parent, an unreleased proprietary hybrid known only by the breeder code 12-60-3 (not patented) and a sibling of 12-60-3 in May of 2014 at an isolation block at a wholesale perennial nursery in Zeeland, Mich. The seeds from the cross were harvested June of 2014 and the single specific seedling that developed into the new *Salvia* was assigned the breeder code 14-27-1 at the end of the evaluation process at the same nursery in the summer of 2015. The first asexual propagation was performed in July of 2016 by basal cuttings at the same nursery in Zeeland, Mich. 'Bumblesnow' has proven that it is stable and reliably produces true to type plants in successive generations of asexual propagation.

SUMMARY OF THE INVENTION

Plants of *Salvia* 'Bumblesnow' have not been observed under all possible environmental conditions. The phenotype may vary somewhat with variations in environment such as temperature, nutrition and light intensity without, however, any variance in genotype.

*Salvia* 'Bumblesnow' can be most closely compared to 'Sensation White' (not patented). The new plant is similar in habit, and flower color, but the new plant is denser with more stems and closer arranged flowers. Comparison with the specific female parent is not possible as the female was not retained. Comparison with the possible male parent, is not possible as the exact male parent is not known or maintained. 'Crystal Blue' has similar stem and flower density but the flower color is light sky blue. 'Bumbleberry' has similar size but the flowers are dark fuchsia pink. 'Bumbleblue' is slightly taller and the flower color is violet-blue. 'Bumblesky' is slightly taller than the new plant and the flower color is light sky blue. 'Snow Hill' ('Schneehugel') (not patented) is taller and looser in habit.

The following characteristics in combination distinguish *Salvia* 'Bumblesnow' as a new and distinct cultivar:

1. Small, strong white-colored flowers densely arranged in tight verticils;

2. Compact rounded habit and stiff, upright, heavily-branched stems;
3. Strong, vigorous and winter-hardy;
4. Small, rugose, gray-green foliage.

BRIEF DESCRIPTION OF THE DRAWINGS

The photographs of the new plant demonstrate the unique traits and the overall appearance of *Salvia* 'Bumblesnow'. The colors are as accurate as reasonably possible with color reproductions. Variation in ambient light spectrum, source and direction may cause the appearance of minor variation in color. The plant used in the photographs was a two-year-old plant grown in an open, full-sun trial garden at a wholesale perennial nursery in Zeeland, Mich. with supplemental water and fertilizer when needed. No stem pinching or plant growth regulators have been used.

DETAILED BOTANICAL DESCRIPTION

Figure 1:
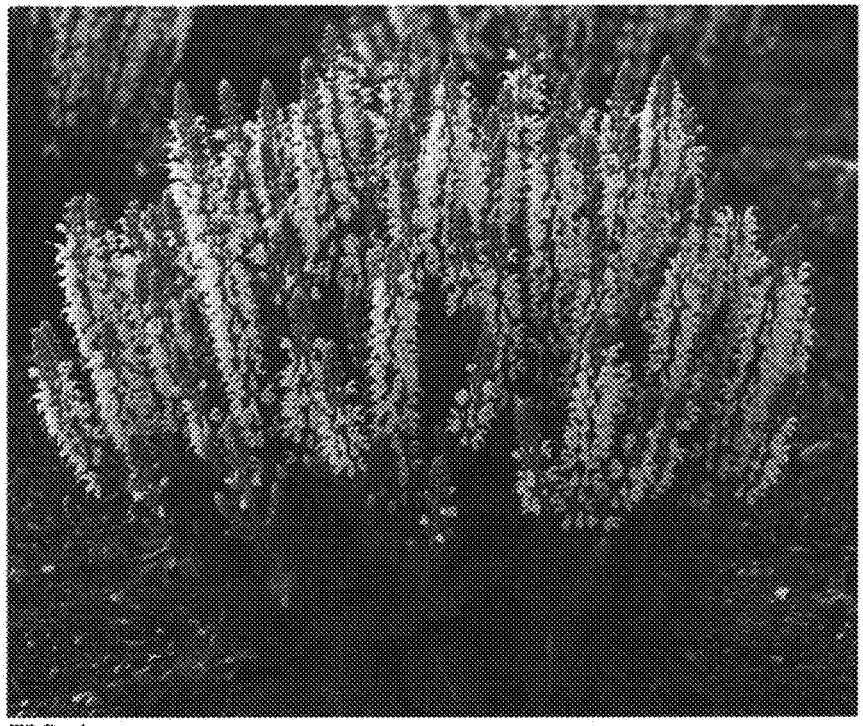
FIG. 1 shows the plant habit in full flower in a landscape.
Figure 2:
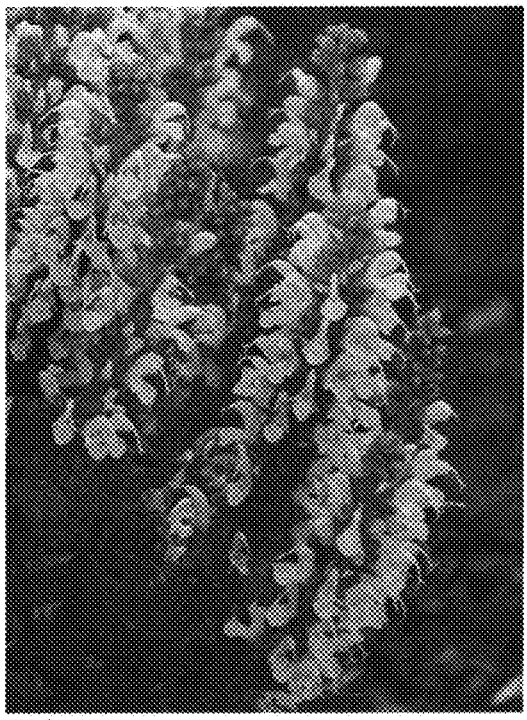
FIG. 2 shows a close-up of the flower scapes with the buds and flowers.

The following descriptions and color references except where common dictionary terms are used are based on the 2015 edition of The Royal Horticultural Society Colour Chart *Salvia* 'Bumblesnow' has not been observed under all possible environments. The phenotype may vary slightly with different growing environments such as temperature, light, fertility, soil pH, moisture and plant maturity levels, but without any change in the genotype. The following observations and size descriptions are based on two-year-old plants growing in an outdoor, full-sun, trial garden at a wholesale perennial nursery in Zeeland, Mich. Plants were given supplemental water and fertilizer but no pinching or plant growth regulators were used.

Botanical classification: *Salvia netnorosa* (Linnaeus);

Parentage: Female or seed parent is the unreleased non-patented proprietary hybrid known as 12-60-3; 12-60-3 is hybrid seedling selection from *Salvia* 'Crystal Blue' U.S. Plant Pat. No. 26,344; the male or pollen parent was a sibling of 12-60-3;

Plant habit: Winter-hardy herbaceous perennial; multi-stemmed, compact, with basal and cauline foliage, and flowers in several tightly arranged verticils on heavily-branched upright racemes displayed above foliage; flowering in heavily-branched panicles to about 30.0 cm tall and about 36.5 cm wide at the fullest point about 18.0 cm above soil; cauline foliage extends about two-thirds of the way up the flowering stems;

Propagation: By herbaceous shoot tip cuttings; time to produce a rooted stems about two weeks;

Growth rate: Rapid, vigorous, finishing in from a 25 mm plug to flower in one-gallon pot in about 10 to 12 weeks, and flowering in a one-gallon pot from a dormant bare-root one-year-old plant in about 6 to 8 weeks;

Root description: Fine, well-branched; color dependent on age and soil type, from cream to dark tan in color;

Foliage: Opposite; simple; slightly rugose; ovate; glabrous to sparsely puberulent abaxial and glabrous adaxial; acute apex and base cordate to rounded; margin crenate; leaf blades about 6.5 cm long and 3.6 cm across, decreasing in size distally; average about 4.8 cm long and 2.2 cm across; foliage is not variegated;

Foliage fragrance: Faint sage fragrance;

Foliage color: Mature adaxial surface nearest RHS 137A, mature abaxial surface between RHS 147B and RHS 146A; expanding adaxial base nearest RHS 144A and distally nearest RHS 137B, expanding abaxial between RHS 138A and RHS 138B;

Venation: Reticulate; impressed on adaxial side and ribbed on abaxial side; puberulent abaxial and glabrous adaxial;

Vein color: Mature adaxial midrib nearest RHS 145D with main and secondary veins nearest RHS 193A near midrib and becoming nearest RHS 137A distally, and mature abaxial midrib and main veins nearest RHS 146D; expanding adaxial midrib nearest RHS 145D with secondary veins nearest RHS 194A and expanding abaxial midrib RHS 145D and secondary veins between RHS 148C and RHS 148D;

Petiole: On basal foliage only; concavo-convex, ciliolate along margin and sparsely puberulent abaxial and adaxial surfaces; to about 3.6 cm long and 3.5 mm wide at base, average 2.8 cm long and 3.0 mm wide at base;

Petiole color: Adaxial center nearest RHS 145C and margins nearest RHS 137C; abaxial center nearest RHS 145C and margins nearest RHS 137C;

Stems: Quadrangular; pubescent, to 7.0 cm long before flowers and 4.0 mm across at base;

Stem color: Nearest RHS 138A;

Nodes: Eight before flowering central flower stem; average internode length 2.2 cm; color same as stem;

Flower: Perfect; bilabiate; zygomorphic; verticillate with flowering generally beginning at lower verticils and advancing up the scape, not all flowers at same verticil opening at the same time; with lower lip prOjected downwardly about 30 degrees below horizontal and hood petal upwardly at about 30 degrees angle above horizontal; self-cleaning, petals not persistent; flowering beginning late spring for about four weeks and repeating if initial scapes removed;

Inflorescence description: Total length about 18 cm tall, flowering in upper 11 cm and branching to about 8 cm wide; average internode distance in flowering portion about 4.0 mm; number of flowers per node or verticil about 10, decreasing distally;

Flower longevity: About four days on the plant;

Flower fragrance: None detected;

Flower buds one to two days prior to anthesis: Ellipsoidal with narrow basal tube, rounded apex; exposed petals puberulent; calyx carinate and micro puberulent; about 6.5 mm long, 2.5 mm tall and 1.5 mm wide;

Flower bud color: Exposed petals nearest RHS 145D; calyx nearest RHS 138A;

Flowers size: About 13.0 mm long from base of calyx to tip of exserted style, 6.5 mm tall and 5.5 mm wide; clustered at verticils with about six flowers per verticil;

Petals: Bilabiate corolla; upper hood projecting upwardly to about 45 degrees from horizontal and lower labium drooping producing an angle between the two petals of about 60 degrees;

Hood (upper) petal: Slightly arcuate to falcate in distal half; vertically conduplicate in distal 7.0 mm, with emarginate apex and basal 6.0 mm fused into tube 2.0 mm diameter at base and 3.0 mm diameter at petal separation; puberulent abaxial, glabrous adaxial; about 9.0 mm long, 3.0 mm tall and 1.0 mm across;

Labium (lower) petal: Abaxial puberulent, glabrous adaxial; consisting of three apical lobes, two upwardly projecting lateral lobes about 3.0 mm long and 1.5 mm wide at base, each lobe with rounded apex; one central, obdeltoid, distally involute lobe, about 3.5 mm long 5.5 mm wide with broadly rounded apex; about 9.0 mm long fused into tube in basal 6.0 mm, 5.5 mm wide at the widest portion and 2.5 mm tall;

Petal color: Abaxial hood distally between RHS NN155A and RHS NN155B, proximally nearest RHS NN155D; adaxial hood nearest RHS NN155C; labium central lobe adaxial and abaxial nearest RHS NN155D with longitudinal center nearest RHS NN155C; labium side lobes adaxial and abaxial nearest RHS NN155D; fused base abaxial proximal region nearest RHS NN155C, adaxial tube nearest RHS NN155C;

Androecium: Two, with diminutive trigger mechanism; fused with labium, contained within hood petal;

*Filaments.*—Two; adnate about 4.0 mm from base of labium petal and curved downward inside hood petal; glabrous; about 1.0 mm long and about 0.2 mm diameter; color nearest RHS NN155C.

*Anther.*—Glabrous, ellipsoidal; about 1.5 mm long and about 0.5 mm diameter; longitudinal, dorsifixed; color blend nearest RHS 158C.

*Pollen.*—Not observed.

*Trigger mechanism; About* 1.0 mm long, curved; color nearest RHS NN155B.

Gynoecium: One, exserted; curved around inside of hood petal; total about 14.0 nm long;

*Style.*—About 11.0 mm long and less than 0.5 mm diameter; color nearest RHS NN155D.

*Stigma.*—Bifid and curved in the terminal 2.0 mm; apex pointed; color nearest RHS NN155D.

*Ovary.*—Superior; about 1.0 mm diameter; color nearest RHS 145A.

*Fruit.*—One to four nutlets per flower; ellipsoidal to spherical; about 1.5 mm diameter; color nearest RHS 202A.

Calyx: Five sepals; three upper and two lower, campanulate, apex acute; fused in basal 3.0 mm; persistent; tube about 5.5 mm long, 4.0 mm tall and 3.0 mm wide; lower cleft about 2.5 mm deep between lobes and upper and lower set; upper set of three fused to closer than 0.5 mm of apex;

Sepal color: Abaxial base nearest RHS 144A with veins and dorsal portion nearest RHS 138A; adaxial base nearest RHS 145A and veins of nearest RHS 138A;

Bracts: Each verticil subtended by two opposite bracts; apex acuminate, base truncate, shape nearly cordate; margin entire, ciliolate, and glabrous above and below; bract size up to 5.0 mm long and 5.0 mm wide, decreasing distally; color of both surfaces nearest RHS 137A near perimeter and center nearest RHS 145D;

Peduncles: Quadrangular in cross section, strong; mostly upright; flowering in peduncle up to 18.0 cm tall and 8.0 cm across; finely puberulent; heavily branched with opposite branches at about 50 to 60 degrees above horizontal at the four nodes below flowers on central stem; branches to about 10.0 cm long and 2.0 mm across; average space between flowers on central stem about 1.5 mm; about 290 flowers per inflorescence; verticils average about 6.0 mm apart closer distally;

Peduncle color: Nearest RHS 138B in upper and lower regions;

Pedicels: Cylindrical; puberulent; about 2.0 mm long and 0.5 mm diameter; horizontal to about 30 degrees above horizontal;

Pedicel color: Nearest RHS 146D;

Disease and pest resistance: Resistance to diseases and pests beyond that common to *Salvia* has not been noted, but the new plant is not commonly browsed by *Cervinea* or *Oryctolagus;*

Growth recommendations: Plants of *Salvia* 'Bumblesnow' perform best with adequate moisture and good drainage but are fairly drought tolerant once established; hardy from USDA zone 3 to 8.

It is claimed:

1. A new and distinct perennial *Salvia* plant named 'Bumblesnow' as herein described and illustrated useful for landscaping as a specimen plant or en masse.

* * * * *